United States Patent [19]
Bungay, III et al.

[11] Patent Number: 5,955,326
[45] Date of Patent: *Sep. 21, 1999

[54] PRODUCTION OF MICROBIAL CELLULOSE USING A ROTATING DISK FILM BIOREACTOR

[75] Inventors: Henry R. Bungay, III; Gonzalo C. Serafica, both of Troy, N.Y.

[73] Assignee: Rensselaer Polytechnic Institute, Troy, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/509,835

[22] Filed: Aug. 1, 1995

[51] Int. Cl.$^6$ .............................. C12P 19/04; C12M 1/14; C08B 15/00
[52] U.S. Cl. .................. 435/101; 435/297.1; 435/297.3; 435/297.5; 435/298.7; 435/298.2; 435/299.1; 536/56; 536/123.1; 536/126
[58] Field of Search .............................. 435/101, 297.1, 435/297.3, 297.5, 298.1, 299.1, 298.2; 536/123.1, 126, 56

[56] References Cited

U.S. PATENT DOCUMENTS

| | | | |
|---|---|---|---|
| 4,320,198 | 3/1982 | Myhatt et al. | 435/101 |
| 4,588,400 | 5/1986 | Ring et al. | 604/304 |
| 4,655,758 | 4/1987 | Ring et al. | 604/374 |
| 4,742,164 | 5/1988 | Iguchi et al. | 536/56 |
| 4,788,146 | 11/1988 | Ring et al. | 435/101 |
| 4,863,565 | 9/1989 | Johnson et al. | 162/150 |
| 4,891,317 | 1/1990 | Brown, Jr. et al. | 435/101 |
| 4,929,550 | 5/1990 | Byrom | 435/101 |
| 4,942,128 | 7/1990 | Brown, Jr. | 435/101 |
| 4,950,597 | 8/1990 | Saxena et al. | 435/101 |
| 4,954,439 | 9/1990 | Brown, Jr. et al. | 435/101 |
| 5,079,162 | 1/1992 | Ben-Bassat et al. | 435/252.1 |
| 5,144,021 | 9/1992 | Arie et al. | 536/56 |
| 5,207,826 | 5/1993 | Westland et al. | 106/163.1 |
| 5,246,854 | 9/1993 | O'Brien et al. | 435/285 |
| 5,256,570 | 10/1993 | Clyde | 435/285 |
| 5,264,129 | 11/1993 | Simpson et al. | 210/611 |
| 5,273,891 | 12/1993 | Byrom | 435/101 |

FOREIGN PATENT DOCUMENTS

| | | | |
|---|---|---|---|
| 1207263 | 7/1986 | Canada | A61L 15/01 |
| 1283099 | 4/1991 | Canada | C08B 15/00 |
| 1295327 | 2/1992 | Canada | C08B 15/00 |
| 62-014787 | 1/1987 | Japan | C12P 1/04 |
| 163664 | 6/1992 | Mexico | C08L 1/002 |
| 2 131 701 | 12/1983 | United Kingdom | A61L 15/03 |

OTHER PUBLICATIONS

ATCC Catalogue of Bacteria and Bacteriophages, 17$^{th}$ Ed., 1989, pp. 1 and 2.
Brown, R. Malcolm, Jr., "Emerging Technologies and Future Prospects for Industrialization of Microbially Derived Cellulose", *American Chemical Society*, p. 77 (1992).
Cannon, Robert E. et al., "Biogenesis of Bacterial Cellulose", *Microbiology*, p. 435.
Hestrin, S., et al., Synthesis of Cellulose by Resting Cells of *Acetobacter xylinum*, *Nature*, 159:64–65.
Masaoka et al., "Production of Cellulose from Glucose by *Acetobacter xylinum*", *Journal of Fermentation and Bioengineering*, 74(1), 18–22 (1993).
Nason, Sheila, "Sweet Treat or New Textile", Rensselaer Polytechnic Institute—*reView*, 16(4), Feb. 10, 1995.
Okiyama et al., "Bacterial cellulose I. Two–stage fermentation process for cellulose production by *Acetabacter aceti*", *Food Hydrocolloids*, 6(5), 471–477 (1992).
Schramm et al., "Factors affecting production of Cellulose at the Air/Liquid Interface of a culture of *Acetobacter xylinum*", *Journal of General Microbiology*, 11:123–129 (1954).
Valla, S., et al., "Cellulose negative mutants of *Acetobacter xylinum*", *Journal of General Microbiology*, 128, 1401 (1982).
Donald G. White and R. Malcolm Brown, Jr., Department of Botony, University of Texas, Austin TX, "Prospects for the Commercialization of the Biosynthesis of Microbial Cellulose", *Commercialization of Microbial Cellulose*, pp. 573–590.
Toyosaki, Hiroshi, et al., "Screening of Bacterial Cellulose–producing Acetobacter Strains Suitable for Agitated Culture", *Biosci. Biotech Biochem*, 59(8), 1502 (1995).

*Primary Examiner*—Francisco Prats
*Attorney, Agent, or Firm*—Darby & Darby

[57] ABSTRACT

A new microbial cellulose with high water content and process for making the new microbial cellulose utilizes a trough containing a biological medium and a cellose producing micro organism. A plurality of disks are partly submerged in the medium and moved through the medium. Cellulose is formed on the surface of the disks which is later harvested.

25 Claims, 6 Drawing Sheets

PRODUCTION OF MICROBIAL CELLULOSE USING A ROTATING DISK FILM BIOREACTOR

FIELD OF INVENTION

The invention relates to the production of microbial cellulose using a rotating disk film reactor. The invention focuses on the concept of using film bioreactors to produce a cohesive pellicle of bacterial cellulose. The film reactor used is a type of rotating disk bioreactor designed for attached growth of extra-cellular cellulose producing organisms and production of a gelatinous microbial cellulose product.

The invention also includes a microbial cellulose product having unique properties, in particular, a highly hydrated pellicle of microbial cellulose. This hydrated cellulose product is characterized by a high ratio (about twice the amount) of water per unit weight of dry cellulose, as compared to bacterial cellulose produced by similar cellulose-producing organisms under static conditions.

The invention also pertains to a method of producing the hydrated bacterial cellulose pellicle by non-static cultivation of cellulose producing organisms in a film bioreactor. The high rate of production of a uniform cohesive gel using a rotating disk bioreactor was unexpected.

BACKGROUND OF THE INVENTION

A number of bacteria, particularly strains of Acetobacter, can be cultivated to produce bacterial cellulose. In the presence of sugar and oxygen, cells of Acetobacter synthesize cellulose extracellularly in the form of fibrils attached to the cell. The fibrils produced by other cells intertwine to form a hydrophilic network known as a pellicle. Typical processes for the production of microbial cellulose have used static cultivation (GB No. 2131701). The pellicle of microbial cellulose is formed on the air/liquid interface of a motionless and undisturbed culture which is usually contained in shallow trays. This coherent gel-like pellicle is desirable for many uses such as a wound dressing, after processing to remove the cells.

Another method of production of bacterial cellulose uses traditional deep-tank stirred bioreactors. Under this agitated condition, a nonpellicular form of bacterial cellulose is produced. This type of production scheme is highly susceptible to strain instability which is demonstrated by the loss of ability to produce cellulose and gradual overgrowth of the cells (Valla, S. and Kjosbakken, J, Cellulose negative mutants of Acetobacter xylinum, *Journal of General Microbiology*, 128, 1401-(1982)). Nevertheless, sustained production of reticulated bacterial cellulose under agitated conditions for over 70 hours has been reported (U.S. Pat. No. 4,863,565) using mutagenized and selected strains.

Also, a four-step process for producing microbial cellulose product (U.S. Pat. No. 5,273,891) involves the use of stirred batch culture. The use of airlift fermentors where air bubbles are used to provide mixing instead of impellers, has also been adapted for bacterial cellulose production (Okiyama, A. Shirae, H., Kano, H. and Yamanaka, S., Bacterial cellulose I. Two-stage fermentation process for cellulose production by *acetobacter aceti*, *Food Hydrocolloids*, 6, No. 5, 471–477. (1992)). Thus, besides undisturbed static cultivation in trays, no alternative bioreactor that is capable of producing coherent membrane pellicles of bacterial cellulose has heretofore been reported.

Although film bioreactors have been common in the wastewater treatment industry for over 20 years, this type of bioreactor configuration is not employed for the production of a biopolymer. The basic idea of film reactors is to attach the growing cells onto a structural element of the reactor to form a film and then promote cell growth either by flowing nutrients across the film or by moving the film contained in the structural element into a nutrient filled vessel. The most popular of this type of film bioreactor is the trickling filter where the film is stationary and media percolates through the film; and the rotating biological contactor (RBC) where the film is dipped into the medium. One known application of this type of film bioreactor besides wastewater treatment is in the production of filamentous fungi (U.S. Pat. No. 5,246,854). This attached growth biological reactor uses a rotating cylinder to which the filamentous fungi attach while the cylinder is partially submerged in a trough filled with nutrient media. While much has been done to promote the use of these conventional film bioreactors for environmental applications, nowhere has it been previously mentioned that the concept of moving a microbial film into a stationary media can be applied in the production of biopolymers such as extracellular cellulose product.

SUMMARY OF THE INVENTION

The present invention at least in part, comprises a method of production for producing a highly gelated microbial cellulose pellicle by culturing cellulose-producing organisms for sustained periods of time under non-static conditions in a rotating disk film bioreactor. The high rate of production of pellicular microbial cellulose is surprising considering past studies stating that mixing normally reduces the amount of cellulose produced (Schramm, M. and Hestrin, S., Factors affecting production of Cellulose at the Air/Liquid Interface of a culture of *Acetobacter xylinum*, Journal of General Microbiology, 11, 123–129. (1954)). Moreover, the high rate of synthesis and highly gelated nature of the inventive microbial cellulose pellicle produced using the rotating disk film bioreactor of the present invention, are entirely unexpected.

The present invention also includes a highly hydrated microbial cellulose product having novel properties. This bacterial cellulose pellicle produced by a rotating disk film bioreactor has twice the amount of water per unit weight of cellulose as compared to bacterial cellulose pellicles produced by cellulose producing organisms under static conditions. This microbial cellulose pellicle can absorb about 200 times its weight in water and has a highly gelated three dimensional structure. Its high water content is due to the new method of production according to the invention.

The macroscopic and microscopic characteristics of the microbial cellulose product produced in accordance with the rotated culture conditions of the invention differ from that produced under known static conditions. Macroscopically, the cellulose produced by the rotating disk film bioreactor forms a highly gelated film about 20 to 30 mm. thick after five days of culture as compared to a 3 to 5 mm microbial cellulose film formed at the air liquid interface of a static culture cultivated for the same amount of time. This continuous pellicle produced using the film reactor also has a more open structure allowing a higher water absorption capacity in comparison with the cellulose product obtained under static conditions. Microscopically, differences are also beleived to exist.

The present invention relates to a process for the production of extracellular microbial cellulose in which a bacterial strain capable of producing extra-cellular microbial cellulose is aerobically cultivated in a culture medium containing a carbon source and other nutrients wherein the process involves the use of a rotating disk film bioreactor. The biological reactor is comprised of:

a) a series of circular disks (although any shape is possible) with the appropriate mesh size that would allow both the attachment and growth of microbial cellulose producing organisms, and the production of extracellular microbial cellulose; the disks being mounted on a shaft to facilitate rotation;

b) a horizontally disposed trough (preferably cylindrical) of sufficient length and depth to contain a biological medium in which at least a portion of the contained disks is submerged when enclosed; the covered trough should also have ports to allow media delivery, aeration/oxygen delivery, inoculation, pH monitoring and sampling; and c) an external rotating means attached to the shaft for rotating the disks contained in the trough.

In accordance with the present invention, the method of producing extracellular microbial cellulose by cellulose producing organisms is as follows:

1) providing a biological reactor vessel as described above;
2) introducing biological medium into the trough;
3) introducing an inoculum of extracellular cellulose producing organism into the trough;
4) rotating the submerged disks contained in the biological reactor at an effective rate;
5) addition of media nutrients, chemicals and polymers, oxygen and monitoring of biological reactor conditions such as pH, whenever necessary; and
6) harvesting the cellulose film formed on the disks by appropriate means.

The process of producing microbial cellulose using a rotating disk film reactor according to the invention has several advantages over the existing processes and current methods of producing microbial cellulose. These advantages of the present invention include large area available for cellulose production, capability of changing medium conditions during cellulose synthesis, high cellulose production rates and easy scale up for large volume production of pellicular microbial cellulose.

Any bacterial strain capable of producing extracellular microbial cellulose maybe used in the process of the invention. Suitable strains include strains belonging to the genus Acetobacter, for instance, *Acetobacter xylinum* strains of the species such as ATCC 10245, 23769, 1082.

A wide range of carbon sources maybe used including lactate, ethanol, glycerol, molasses, sucrose and other sugars such as fructose and particularly glucose. Suitable initial carbon source concentration are within the range of 2 to 100 gm/liter. Sugar can be added to the growing culture in the reactor to maintain a certain desirable concentration for optimum cellulose production. For large scale production, various feedstocks for nitrogen sources can utilized including corn steep liquor.

The initial pH at which to cultivate the cellulose producing organism according to the invention is between 3 to 6 with the preferred range of 4.5 to 5.5 and most preferably at 5.0. The pH in the bioreactor can be controlled by means of buffers such as citrate, or by the addition of base or acid to the medium to maintain the pH in the desired range.

The air supply to the reactor can be varied in its composition from air (21% oxygen) to 100% oxygen and in its feed flow rate depending on what is best for the production of microbial cellulose. Maintenance of a positive pressure of oxygen inside the bioreactor to increase rates of production and prevent contamination.

The rotational speed is usually dependent on the size or diameter of the disk used in the biological reactor. As an example, for a 12 cm. diameter disk, the rotational speed should be between the range of 1 to 30 rpm with 6 to 12 rpm being preferable. The rotational speed of the disks during cellulose production has a noticeable effect on the production rate of cellulose during the fermentation.

The modes of operating the biological reactor can be by batch fermentation, fed batch fermentation and continuous fermentation, with each having its own advantages. Batch fermentation may be sufficient for producing pellicular microbial cellulose for bulk applications. Fed-batch fermentation or continuous processing may be desirable especially in the production of modified or composite microbial cellulose pellicles.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
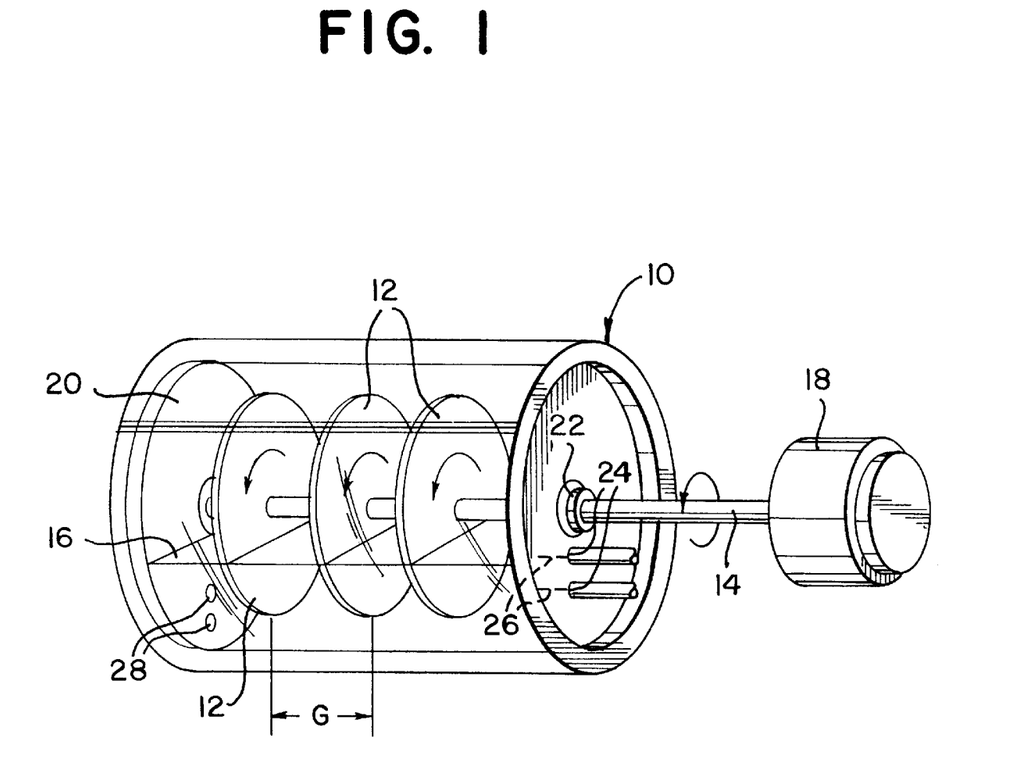
FIG. 1 is a perspective view of the rotating disk film bioreactor with microbial cellulose pellicle forming on the disks, according to the present invention.

In the following detailed description of the invention particulars of the rotating disk film bioreactor shown in FIG. 1, are discussed. The type of disk 12 that is used in the biological reactor 10 for the invention has an appropriate mesh size to allow bridging between the two films developing on both sides of the disk. It is preferred, for practice of the present invention, that the disk be in the form of a mesh or perforated plate, made up of stainless steel or polymeric materials with sufficient rigidity. The size or diameter of the disk is a selected percentage of the diameter of the cylinder 20 of the cylindrical biological reactor 10 that contains the disk, with 80% to 90% of the diameter of the cylindrical trough being desirable. The gap between the disks 12 mounted on the shaft 14, labelled "G", is as small as possible to maximize the available area for growth of the cellulose producing organism and production of microbial cellulose by these organisms. The limit of this gap width is the eventual thickness of the bacterial cellulose pellicle at the end of the fermentation.

The cylindrical shape of the biological reactor 10 is chosen to minimize the amount of biological medium 16 required to wet the rotating disk during rotation. Scale up of the rotating disk film bioreactor can be done by increasing either the length of the cylindrical trough or cylinder 20, or the diameter of the cylindrical trough, or both. This correspondingly increases the number of disks 12 and available surface area for cell growth and cellulose production contained in the biological reactor.

The shaft 14 that connects and holds the disks 12 contained in the cylindrical trough 20 is located on the center of the disks but could be along the disk's periphery if there were on assembly of disks. A hermetically sealing bearing 22 is used to connect the shaft 14 to an externally positioned rotating device 18. The preferred rotating means is an electric motor. The speed of rotation of the disks 12 contained in the biological reactor 10 should be an effective rate which is partially dependent on the diameter of the disk used. Suitable rotational speeds range from 1 rpm to 60 rpm, preferably between 6 to 12 rpm. Any suitable collective mechanism, such as assortment of gears, to operate several rotating shafts mounted with disks contained in several cylindrical biological reactors, using one motor can be provided for multiple reactor operation. Such a configuration of multiple biological reactors can increase the overall production capacity.

The cylindrical trough 20 of the present invention has openings 24 for the attachment of probes 26 for measurement of reactor conditions such as a pH and temperature. The openings can be located on the lower half of the cylindrical trough 20 containing the biological medium 16. Sample and draining ports 28 are also incorporated in the design. The overall construction of the biological reactor in this invention can be made airtight so as to allow oxygen delivery, thereby maintaining a positive pressure inside the reactor for increased cellulose production (Schramm, et al., 1954) and prevent contamination of non sterile air outside.

The use of the rotating disk film bioreactor has several advantages over the existing processes and methods of producing microbial cellulose. The present invention besides having the ability to produce a pellicular microbial cellulose, has the capability of modifying the cellulose film while it is being synthesized in the bioreactor. By controlling the media conditions and composition, it is not only possible to optimize the cellulose production in the biological reactor but also enables incorporation of different types of polymers/additives to the developing cellulose pellicle. Such modifications in the medium would be very difficult to implement in a static system of cultivation. The addition of polymers/additive to the growing continuous layers cellulose can more easily be accomplished in the rotating disk film reactor than in stirred deep-tank bioreactor systems of the prior art. The formation of cellulose by extracellular cellulose producing organism occurs at the air liquid interface and cellulose production is directly proportional to the area of the said interface (Masaoka, S., Ohe, T. and Sakota, N. Production of Cellulose from Glucose by *Acetobacter xylinum*, Journal of Fermentation and Bioengineering, 74 No.1, 18–22 (1993)). The present invention provides an order of magnitude larger surface area to liquid volume ratio available for bacterial cellulose film growth as compared to static methods of cultivation. Scale up of the present invention can be accomplished easily by increasing the length of the cylindrical trough or by using a larger diameter disk thereby increasing the area for cell growth and cellulose production. The modular nature of the biological reactor described in this invention permits the increase in production capacity by increasing the number of modules/bioreactors in service. Losses due to contamination can then be minimized by this modular design of the present invention.

Any bacterial strain capable of producing extra-cellular microbial cellulose maybe used in the process of the invention. Suitable strains include belonging to the genus *Acetobacter* for instance strains of the species *Acetobacter xylinum*, such as strains ATCC 10245, 23769. The inoculum can be prepared by incubating the extracellular cellulose producing organism obtained from a growing culture on agar slant in a suitable medium at an effective temperature of about 25 to 35° C. preferably at 30. Incubation times range from three to five days depending on the size of the inoculum used. After incubation, the resulting microbial cellulose pellicle is macerated to release the cellulose producing cells. Prior to its addition to the reactor, the inoculum is usually centrifuged or filtered to separate the cells from the cellulose. The media for the reactor may be separately sterilized in an autoclave under appropriate conditions for an effective period of time to obtain substantial sterilization. The entire biological reactor and the contents can be placed in a temperature controlled room at an appropriate temperature, preferably at 30° C. A sterile oxygen containing gas can be introduced to the reactor during growth of the extracellular cellulose producing organism and production of microbial cellulose by these organism.

When operating the biological reactor in fed batch mode, additional medium is introduced into the reactor during the course of the fermentation. Depending on the requirements of the product to be produced in the reactor, the medium composition and condition can be changed accordingly. If a continuous fermentation is desired, after the cellulose film has sufficiently formed on the disks, the cellulose produced can scraped off and harvested. The run can then be continued to allow growth and attachment of the cellulose producing organism onto the disk. Additional nutrient and inoculum maybe added depending on the demands of the reactor. The operating conditions such as rotational speed and pH are outlined in the Summary of the invention.

Having thus described the invention, the following examples are presented for illustrative purposes only and should not be taken as limiting the invention in any way.

EXAMPLE 1

Comparison of Cellulose Production in Static Cultures and in a Rotating Disk Film Bioreactor (RDFB)

The extracellular cellulose producing microorganism is a strain of *Acetobacter xylinum* obtained from National Science and Research Institute at University of Philippines, Quezon City, Philippines. The microorganism is maintained on tomato serum broth in agar slants and transferred monthly. The composition of the maintenance culture (TSB) medium is as follows, 50 g/l sucrose or glucose, 5 g/l yeast extract, 5 g/l bactopeptone, 10% v/v tomato serum, 1 g/l $K_2HPO_4$, 0.2 g/l $MgSO_4.7H_2O$, and 0.1 g/l NaCl, pH=5. The rate of cellulose production in tomato serum broth (TSB) is checked regularly to make sure no mutation or contamination has occurred.

Seed test tubes containing 25 ml of 50 g/l glucose, 5 g/l bactopeptone, and 5 g/l yeast extract (GYP medium) are inoculated from agar slants. The test tube cultures are grown for three days at 30° C. without shaking and then transferred in a 250 Erlenmeyer flask containing 150 ml of GYP medium. After 3 days of static culture, the seed flasks is used to inoculate both static flask cultures and the rotating disk film reactor at a level of 15% v/v.

Some of the inoculated GYP medium is transferred to the static culture flasks that serve as controls and the rest is used to fill the rotating disk film bioreactor to the halfway mark. Both static and rotated cultures are incubated at 30° C. and samples are taken each day.

Figure 2:
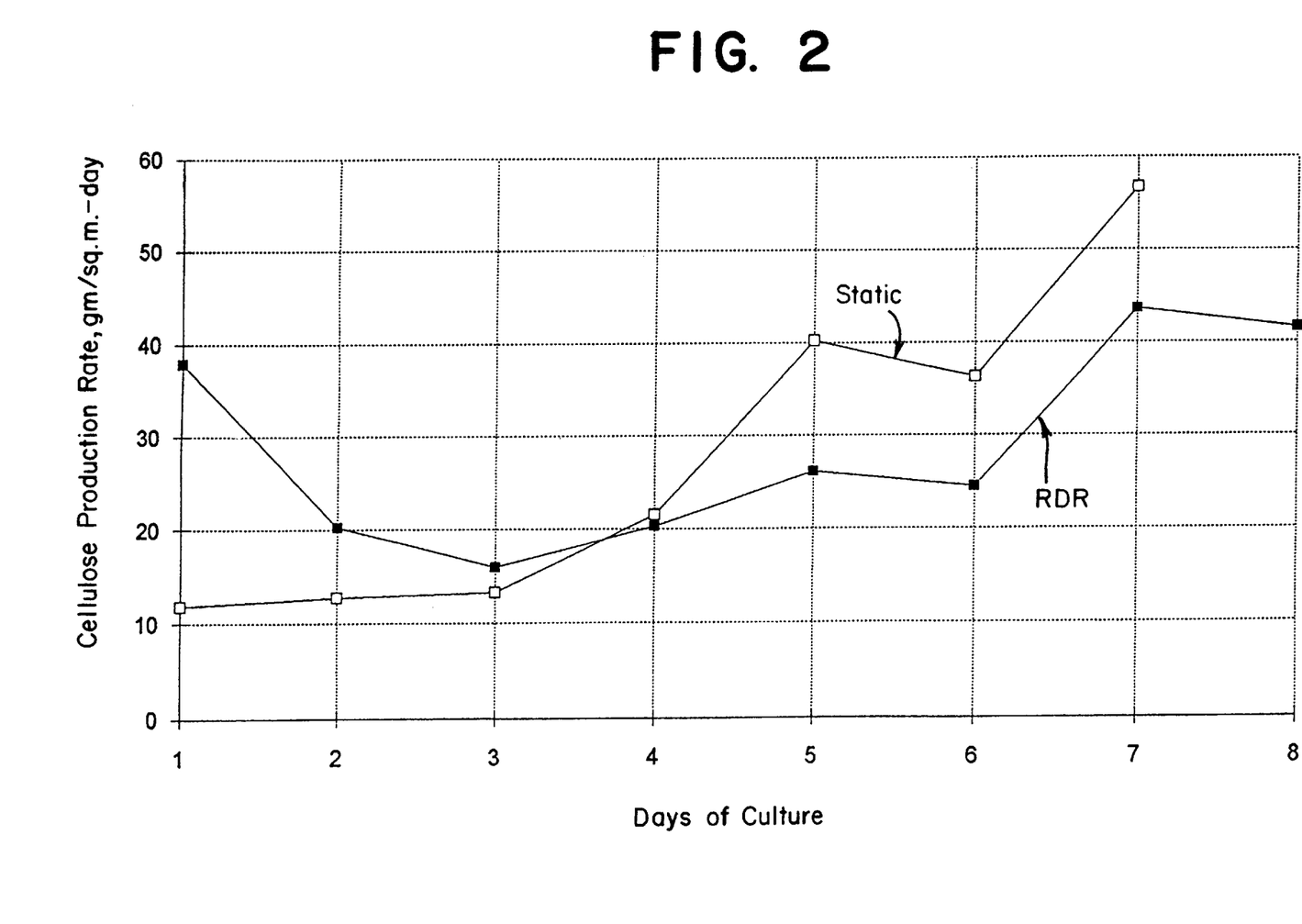
FIG. 2 is a graph showing the linear relation between time of culture and amount of cellulose produced in the rotating disk film bioreactor (RDR) and in a static culture.

To measure the cellulose production, the pellicle in the static culture and the film formed in the rotating disk are harvested and then washed with deionized water. Both are then suspended in a hot 2% NaOH solution for 30 minutes to disintegrate the cells embedded in the pellicle. The wet cellulose pellicles are then soaked in deionized water until the color becomes white or transparent and then dried overnight at 55° C. The resulting dried cellulose films are weighed (data shown in FIG. 2).

EXAMPLE 2

Comparison of Water Content of Static and Rotating Disk Bioreactor Microbial Cellulose Product The water content of the microbial cellulose produced by the two processes were compared by measuring the wet weight and the dry weight of the two cellulose products. The microbial cellulose pellicles for this study are obtained from a five day old culture using GYP medium. After harvesting the pellicles in both the static and rotating bioreactor, the cellulose products are cleaned using deionized water and 2% NaOH as previously mentioned.

The wet weight of the microbial cellulose product is measured by draining the water-soaked pellicle for five minutes and then taking the weight. The dry weight is measured after drying the wet pellicle at 55° C. overnight. The results suggest that typically, microbial cellulose obtained under static conditions has a ratio of dry cellulose to wet cellulose of about 1:100. The microbial cellulose produced by the rotating disk bioreactor has a ratio of 1:200, showing that it is more gelated and has a higher water absorbing capacity than the statically grown pellicle.

| Process | Sample 1 | | Sample 2 | | Sample 3 | |
|---|---|---|---|---|---|---|
| Weight (gms) | Wet | Dry | Wet | Dry | Wet | Dry |
| Static | 16.31 | 0.148 | 37.07 | 0.361 | 84.5 | 0.832 |
| Rotating Disk | 191.4 | 1.07 | 201.9 | 1.08 | 157.6 | 0.696 |

EXAMPLE 3

Effect of Rotational Speed on Cellulose Production in a RDFB

Figure 3:
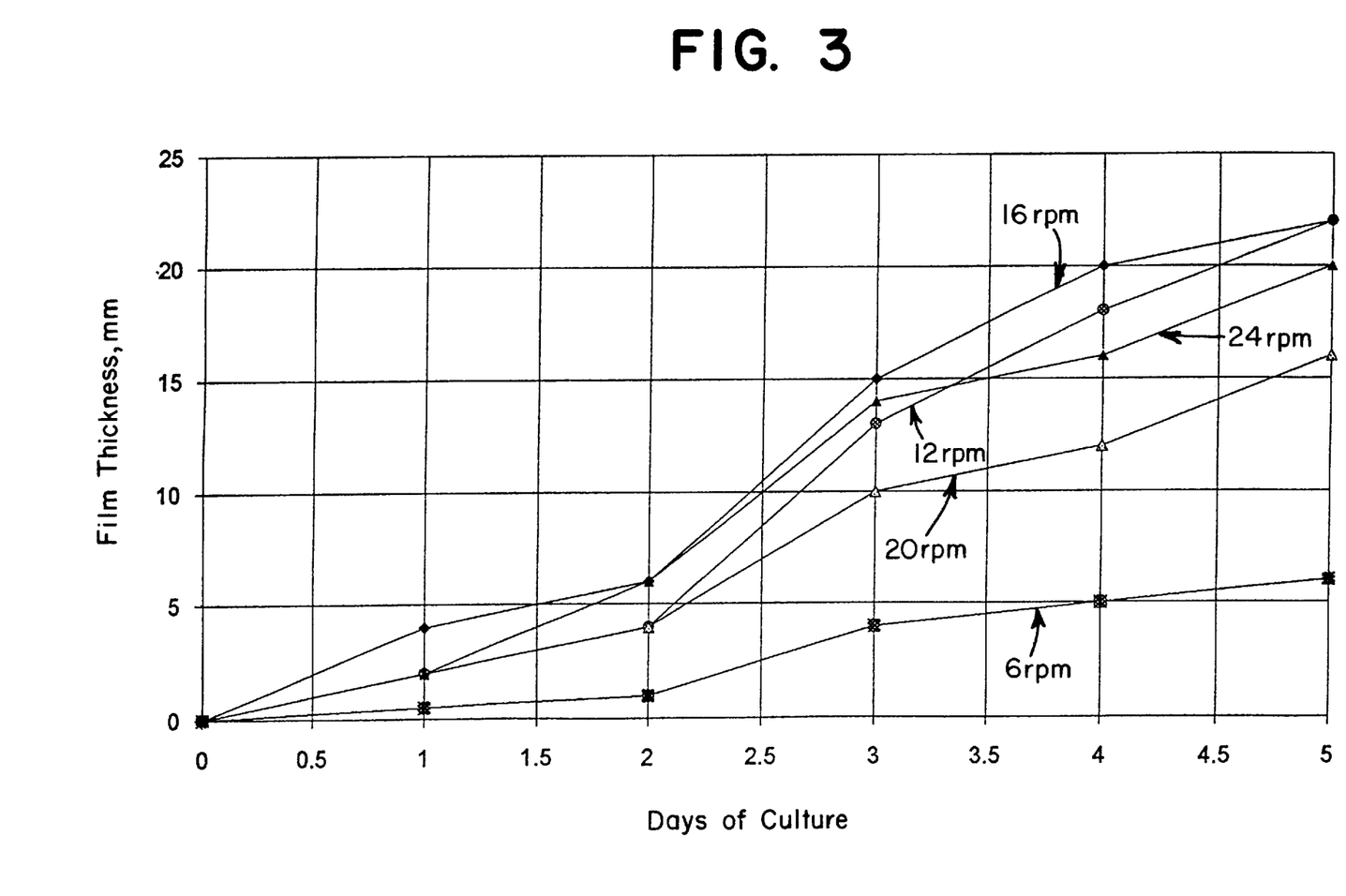
FIG. 3 is a graph showing the effect of rotational speed of the disks in the rotating disk film bioreactor on the production rate of microbial cellulose.

Several 1-liter Rotating Disk Bioreactors were charged with the same inoculated GYP medium and were incubated at 30° C. Each reactor has a different rotational speed falling in the range of 2 to 30 rpm. The thickness of the developing film which is in direct proportion to the amount of cellulose product produced was measured for each rotational speed on a daily basis. The results as shown in FIG. 3, indicate that for the size of the disk used in all the reactors (12 cm. diameter), the speed of rotation displaying fast film growth is between 12 to 20 rpm, preferably 12 rpm. Although an optimum speed for a 12 cm disk was found, such desirable rotational speed may vary depending on the size of the disk being used. Calculating the peripheral velocity of each disk size can help in determining the appropriate rotational speed for a given size of disk.

EXAMPLE 4

Effect of Different Initial Sugar Concentration on Cellulose Production

Figure 4:
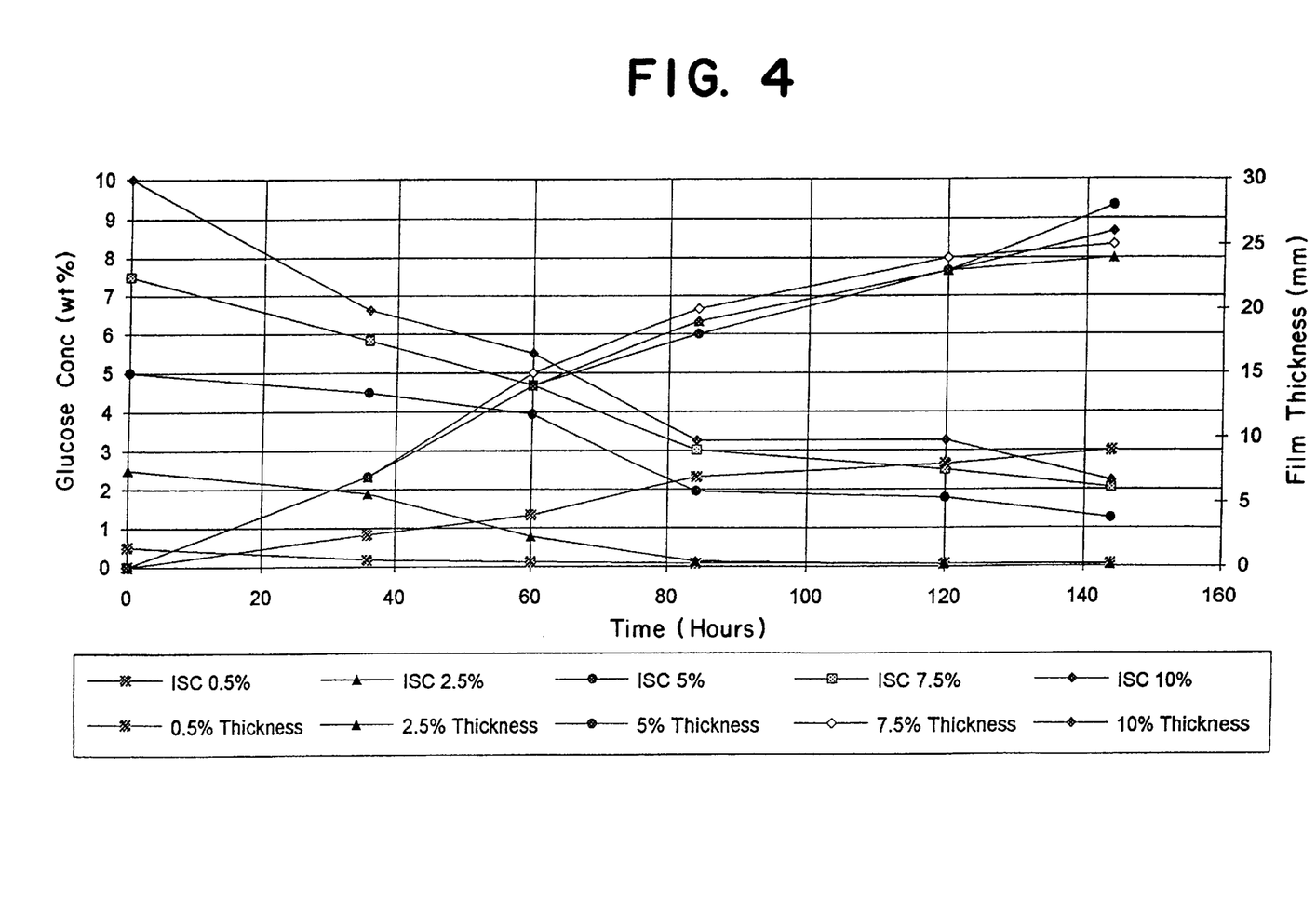
FIG. 4 is a graph showing the effect of initial sugar concentration in the rotating disk film bioreactor on the production rate of microbial cellulose.

The effect of starting sugar concentration in the medium on cellulose production in a batch rotating disk bioreactor was studied. Several reactors containing medium with different initial sugar concentration ranging from 5 g/l to 100 g/l were operated for five days. With all other components being the same, the rate of production of cellulose was compared in each bioreactor by measuring the thickness of the film developed in the disks. As previously mentioned, the film thickness is directly proportional to the amount of cellulose produced. In FIG. 4, the results showed that above 25 g/l, increasing the sugar concentration does not correspond to an increase in cellulose production during the five day culturing time. However, an inadequate amount of sugar as in the case of 5 g/l, can hamper cellulose production. Therefore, in order to maximize the amount of cellulose produced, a certain amount of sugar concentration should be maintained in the bioreactor all through the fermentation. Such a maintenance sugar concentration lies between 5 g/l and 25 g/l.

EXAMPLE 5

Figure 5:
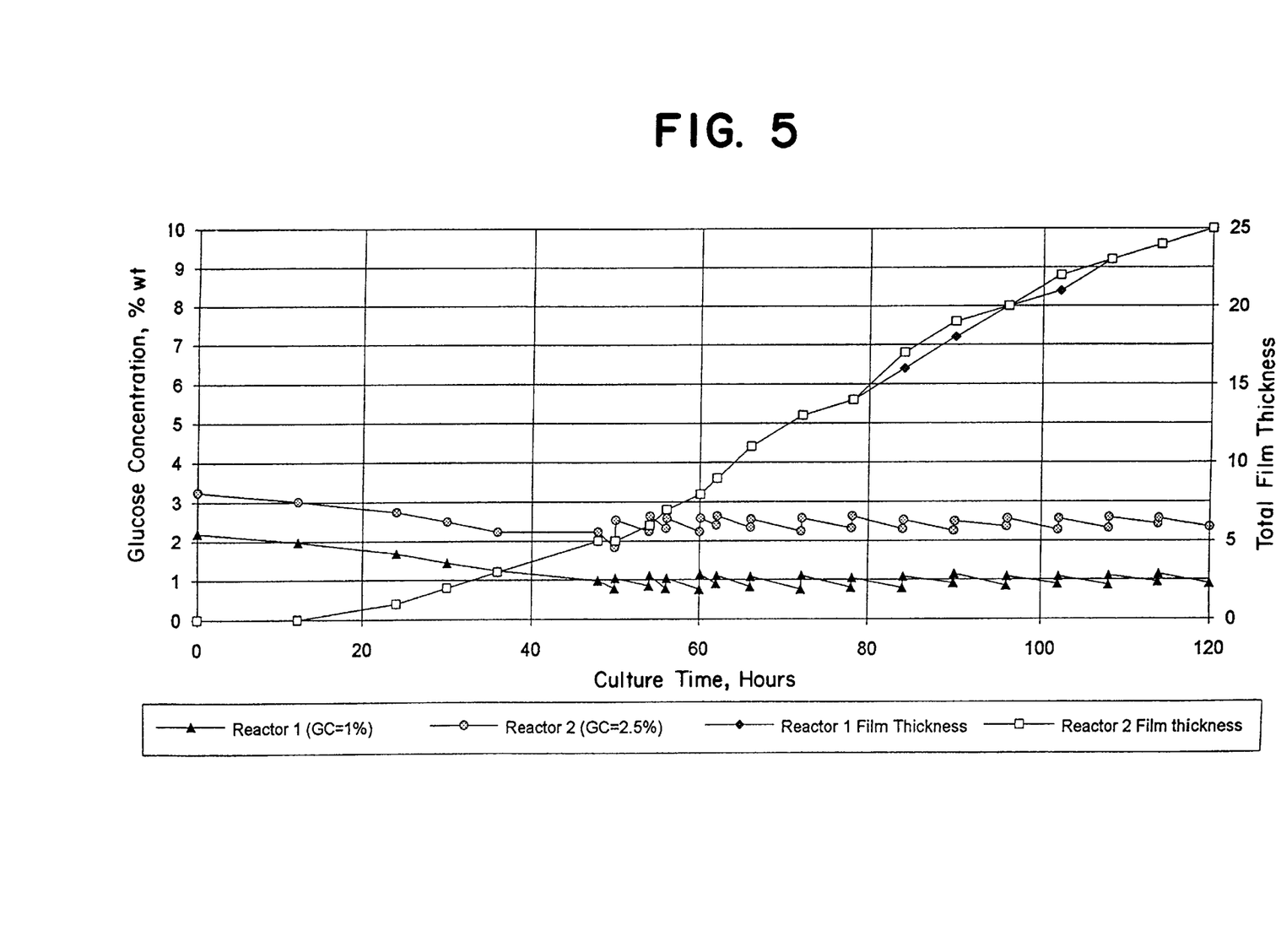
FIG. 5 is a graph of sugar concentration and cellulose film growth during a Fed batch operation of the rotating disk bioreactor.

Fed Batch Operation of the Rotating Disk Bioreactor with Control of Sugar Concentration The rotating disk bioreactor is operated in fed-batch mode wherein sugar is added during the course of the fermentation in order to maintain a certain level of sugar concentration in the reactor. For our purpose, two reactors are operated simultaneously, one having a maintained sugar concentration of 25 g/l and the other at 10 g/l. The sugar concentrations are monitored using a YSI glucose analyzer. Based on the two runs performed (FIG. 5), similar cellulose production rates are observed for both maintained concentration as shown by almost similar rate of film growth on the disks. In order to reduce the amount of sugar wasted, thereby increasing the yield of cellulose per gm of sugar, a concentration of 10 g/l in the bioreactor is preferred.

EXAMPLE 6

Figure 6:
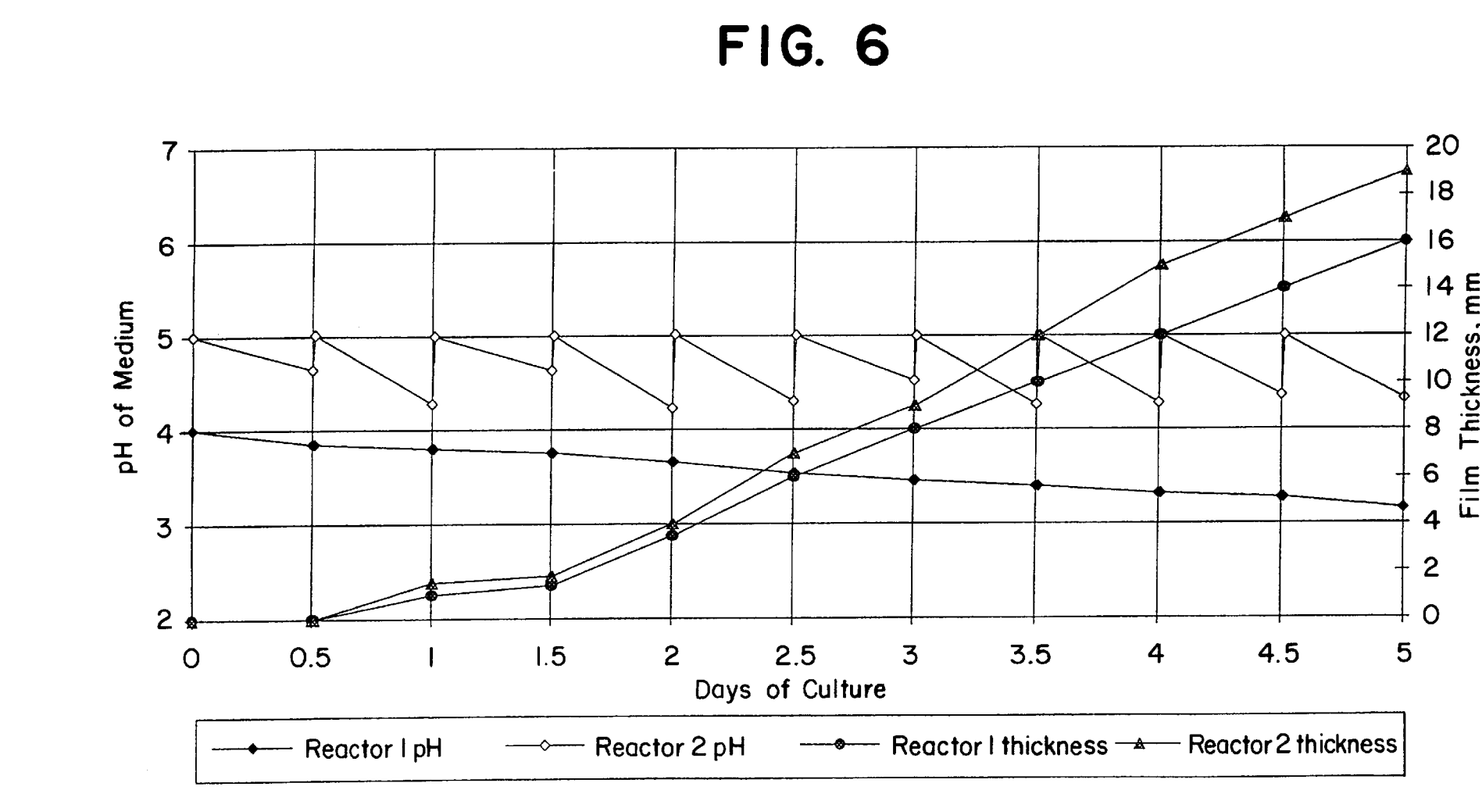
FIG. 6 is a graph showing the effect of operating pH on cellulose production during batch operation of the rotating disk bioreactor.

Effect of Operating pH on Cellulose Production during Batch Operation of the Rotating Disk Bioreactor The rate of cellulose production is very much affected by the operating pH of the medium (Masaoka, 1993). In order to show this effect in the bioreactor, two 1 li rotating disk bioreactors are operated simultaneously, one having a pH maintained at pH 5 and the other without pH control. The pH adjustment is accomplished by the addition of base like dilute NaOH during the fermentation run. The measured rate of film growth is used to indicate the rate of cellulose production as done previously. From FIG. 6, the results show that higher cellulose production can be obtained by maintaining the operating pH in the reactor at the desirable level such as pH 5.

While a specific embodiment of the invention has been shown and described in detail to illustrate the application of the principles of the invention, it will be understood that the invention may be embodied otherwise without departing from such principles.

What is claimed is:

1. A method for producing a composition comprising cellulose, wherein said cellulose consists of a pellicular microbial cellulose, said process comprising (a) aerobically incubating a cellulose-producing microorganism in a rotating disk bioreactor to produce said pellicular cellulose, wherein said bioreactor comprises a plurality of disks mounted on a rotatable shaft, said disks having a mesh size adapted for attachment and production of extra-cellular microbial cellulose; wherein said cellulose producing microorganism is attached to one or more of said disks; and wherein said disks rotate alternately to submerge said cellulose-producing microorganism in a liquid and to pass said cellulose-producing microorganism through a gas medium containing oxygen; and wherein the ratio of rotational speed of said disks in rpm to the diameter of said disks in centimeters ranges from 1/12 to 5/2.

2. A method as defined in claim 1, further comprising (b) collecting said pellicular cellulose.

3. A method as defined in claim 1, wherein said reactor further comprises a trough adapted to contain medium and for submerging at least a portion of said disks; and a rotary drive attached to said shaft.

4. A method as defined in claim 1, wherein said microorganism belongs to the genus Acetobacter.

5. A method as defined in claim 4, wherein said microorganism belongs to the species *Acetobacter xylinum*.

6. A method as defined in claim 5, wherein said microorganism is selected from the group consisting of *Acetobacter xylinum* strains ATCC 10245 and ATCC 23769.

7. A method as defined in claim 1, wherein said pellicular cellulose comprises a film.

8. A method as defined in claim 1, wherein said pellicular cellulose has a cellulose:water absorbed weight ratio ranging from about 1:178 to about 1:226.

9. A method as defined in claim 8, wherein said ratio is 1:200.

10. A method as defined in claim 7, wherein said film has a thickness ranging from about 20 to 30 mm.

11. A method as defined in claim 1, wherein said method is conducted by a process selected from the group consisting of batch processing, fed batch processing, and continuous processing.

12. A method as defined in claim 1, wherein said medium comprises an additive to be incorporated into said pellicular cellulose.

13. A method as defined in claim 1, wherein said medium comprises a polymer to be incorporated into said pellicular cellulose.

14. A method for producing a composition comprising cellulose, wherein said cellulose consists of highly hydrated microbial cellulose having a cellulose:absorbed water weight ratio ranging from about 1:178 to about 1:226, said process comprising (a) aerobically incubating a cellulose-producing microorganism in a rotating disk bioreactor to produce said hydrated cellulose, wherein said bioreactor comprises a plurality of disks mounted on a rotatable shaft, said disks having a mesh size adapted for attachment and production of extra-cellular microbial cellulose; wherein said cellulose producing microorganism is attached to one or more of said disks; and wherein said disks rotate alternately to submerge said cellulose-producing microorganism in a liquid and to pass said cellulose-producing microorganism through a gas medium containing oxygen.

15. A method as defined in claim 14, further comprising (b) collecting said hydrated cellulose.

16. A method as defined in claim 14, wherein said reactor further comprises a trough adapted to contain medium and for submerging at least a portion of said disks; and a rotary drive attached to said shaft.

17. A method as defined in claim 14, wherein said microorganism belongs to the genus Acetobacter.

18. A method as defined in claim 17, wherein said microorganism belongs to the species *Acetobacter xylinum*.

19. A method as defined in claim 18, wherein said microorganism is selected from the group consisting of *Acetobacter xylinum* strains ATCC 10245 and ATCC 23769.

20. A method as defined in claim 14, wherein said highly hydrated cellulose comprises a film.

21. A method as defined in claim 20, wherein said film has a thickness ranging from about 20 to 30 mm.

22. A method as defined in claim 14, wherein said method is conducted by a process selected from the group consisting of batch processing, fed batch processing, and continuous processing.

23. A method as defined in claim 14, wherein said medium comprises an additive to be incorporated into said highly hydrated cellulose.

24. A method as defined in claim 14, wherein said medium comprises a polymer to be incorporated into said highly hydrated cellulose.

25. The method of claim 1 wherein the ratio of disk rotational speed in rpm to disk diameter in centimeters ranges from 1/2 to 1.

* * * * *